US008581001B2

(12) United States Patent
DiMauro

(10) Patent No.: US 8,581,001 B2
(45) Date of Patent: Nov. 12, 2013

(54) METFORMIN-CYSTEINE PRODRUG

(75) Inventor: Thomas M. DiMauro, Raynham, MA (US)

(73) Assignee: Codman & Shurtleff, Raynham, MA (US)

( * ) Notice: Subject to any disclaimer, the term of this patent is extended or adjusted under 35 U.S.C. 154(b) by 94 days.

(21) Appl. No.: 13/087,673

(22) Filed: Apr. 15, 2011

(65) Prior Publication Data
US 2011/0257432 A1 Oct. 20, 2011

Related U.S. Application Data

(60) Provisional application No. 61/325,204, filed on Apr. 16, 2010.

(51) Int. Cl.
C07C 323/58 (2006.01)
C07C 323/59 (2006.01)
(52) U.S. Cl.
CPC ............. *C07C 323/58* (2013.01); *C07C 323/59* (2013.01)
USPC .......................................................... 562/557
(58) Field of Classification Search
CPC ............................ C07C 323/58; C07C 323/59
See application file for complete search history.

(56) References Cited

U.S. PATENT DOCUMENTS

| | | | |
|---|---|---|---|
| 5,955,106 | A | 9/1999 | Moeckel |
| 6,031,004 | A | 2/2000 | Timmins |
| 6,099,859 | A | 8/2000 | Cheng |
| 6,100,300 | A | 8/2000 | Rogosky |
| 6,107,317 | A | 8/2000 | Villhauer |
| 6,120,803 | A | 9/2000 | Wong |
| 6,124,305 | A | 9/2000 | Villhauer |
| 6,340,475 | B2 | 1/2002 | Shell |
| 6,475,521 | B1 | 11/2002 | Timmins |
| 6,491,950 | B1 | 12/2002 | Gutierrez Rocca |
| 6,790,459 | B1 | 9/2004 | Cheng |
| 6,923,988 | B2 | 8/2005 | Patel |
| 6,946,146 | B2 | 9/2005 | Mulye |
| 6,960,357 | B2 | 11/2005 | Chopra |
| 2002/0132002 | A1 | 9/2002 | Gutierrez Rocca |
| 2003/0021841 | A1 | 1/2003 | Matharu |
| 2003/0220301 | A1 | 11/2003 | Lal |
| 2004/0175424 | A1 | 9/2004 | Castan |
| 2004/0213844 | A1 | 10/2004 | Massironi |
| 2005/0158374 | A1 | 7/2005 | Wong |
| 2007/0154548 | A1 | 7/2007 | Cheng |
| 2007/0264331 | A1 | 11/2007 | Regalado |
| 2007/0275061 | A1 | 11/2007 | Jo |
| 2009/0124702 | A1 | 5/2009 | Siva Satya Krishna Babu |

FOREIGN PATENT DOCUMENTS

| | | |
|---|---|---|
| JP | 2002326927 | 11/2002 |
| WO | 9515309 | 6/1995 |
| WO | 9731907 | 9/1997 |
| WO | 9818736 | 5/1998 |
| WO | 9819998 | 7/1998 |
| WO | 9961431 | 12/1999 |
| WO | 0006129 | 2/2000 |
| WO | 0103964 | 1/2001 |
| WO | 0247607 | 3/2003 |

OTHER PUBLICATIONS

Huttunen et al, Journal of Medicinal Chemistry, The First Bioreversible Prodrug of Metformin with Improved Lipophilicity and Enhanced Intestinal Absorption, 2009, 52, pp. 4142-4148.*
Guarino et al, Bioorganic & Medicinal Chemistry Letters, Sulfenamides as Prodrugs of NH-acidic Compounds: A New Prodrug Option for the Amide Bond, 2007, 17, pp. 4910-4913.*
Oliveira et al, Hepatology Research, Combination of N-Acetylcysteine and Metformin Improves Histological Steatosis and Fibrosis in Patients with Non-alcoholic Steatohepatitis, 2008,38, pp. 159-165.*
Liu et al, Chemico-Biological Interactions, the Antidiabetic Effects of Cysteinyl Metformin, A Newly Synthesized Agent, in Alloxan- and Streptozocin-induced Diabetic Rats, 2008, 173, pp. 68-75.*
Barton, A 'One-Pot' Synthesis of Sulfenamides, *J. Org. Chem.*, 1991, vol. 56, pp. 6702-6704.
Berkeley, "Hepatoprotection by L-Cysteine-Glutathione Mixed Disuldfide, A Sulfhydryl-Modified Prodrug of Glutathione", *J. Biochem. Molec. Toxicology*, 2003, vol. 17, No. 2, pp. 95-97.
Cacciatore, "Prodrug Approach for Increasing Cellular Glutathione Levels", *Molecules*, 2010, vol. 15, pp. 1242-1264.
Dilger, "Oral N-acetyl-l-cysteine is a safe and effective precursor of cysteine", *J. Anim. Sci.* 2007, vol. 85, pp. 1712-1718.
Guarino, "Sulfenamides as prodrugs of NH-acidic compounds: A new prodrug option for the amide bond", *Bioorg. & Medicinal Chemistry Letters*, 2007, vol. 17, pp. 4910-4913.
Holst, "Inhibition of the Activity of Dipeptidyl-Peptidase IV as a Treatment for Type 2 Diabetes", 1998, *Diabetes*, vol. 47, pp. 1663.
Huttunen, "The First Bioreversible Prodrug of Metformin with Improved Lipophilicity and Enhanced Intestinal Absorption", *J. Med. Chem.*, 2009, vol. 52, Issue 14, pp. 4142-4148.
Kickstein, "Biguanide metformin acts on tau phosphorylation via mTOR/protein phospat (PP2A) signaling", *Proc Natl Acad Sci USA*, Dec. 14, 2010; vol. 107, Issue 50, pp. 21830-21835.
Li, Identification of Stereoselective Transporters for S-Nitroso-L-cysteine *J. Boil. Chem.*, 2005, vol. 280, Issue 20, 20102-20110.

(Continued)

Primary Examiner — Paul A Zucker

(57) ABSTRACT

A metformin-cysteine prodrug. It is believed that the prodrug of the present invention will transport in the LAT1 and LAT2 transporter system. Because the LAT1 and LAT2 transporters are important and effective transporters of amino acids in both the small intestine and colon, it is believed that the LAT-transportable prodrugs of the present invention will be effectively absorbed both in small intestine and in the colon. The increased absorption window provided by the present invention should result in highly sustained plasma concentrations of metformin, thereby increasing the effectiveness of the medication and allowing for a single daily dose.

2 Claims, 3 Drawing Sheets

(56) References Cited

OTHER PUBLICATIONS

Li, "Dietary supplementation with cysteine prodrugs selectively restores tissue glutathione levels and redox status in protein-malnourished mice1", *J. Nutr., Biochem.*, Oct. 2002; vol. 13, Issue 10, pp. 625-633.

Marathe "Effect of altered gastric emptying and gastrointestinal motility on metformin absorption" *Br. J. Clin., Pharmacol.*, 2000, vol. 50, pp. 325-332.

Masha, "N-acetylcysteine is able to reduce the oxidation status and the endothelial activation after a high-glucose content meal in patients with Type 2 diabetes mellitus", *J. Endocrino.Invest.*, Apr. 2009, vol. 32, Issue 4, pp. 352-356—Abstract.

McCaddon, "L-methylfolate, methylcobalamin, and N-acetylcysteine in the treatment of Alzheimer's disease-related cognitive decline,", CNS Spectr. Jan. 2010; vol. 15 (1 Suppl 1), pp. 2-5—Abstact.

Philbrick, "Metformin use in renal dysfunction: is a serum creatinine threshold appropriate?" *Am. J. Health Syst. Pharm.*, Nov. 2009 vol. 15; 66 (22), pp. 2017-2023—Abstract.

Pinto, "Combination of N-acetylcysteine and metformin improves histological steatosis and fibrosis in patients with non-alcoholic steatohepatits", *Hepatology Research*, 2008, vol. 38, pp. 159-165.

Saklayen, "Effect of month-long treatment with oral N-acetylcysteine on the oxidative stress and proteinuria in patients with diabetic nephropathy: a pilot study", *J Investig Med.*, Jan. 2010, vol. 58, Issue 1, pp. 28-31.

Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats", *J. Pharmacol. Experimental Therap.*, 2004, vol. 310, No. 2, pp. 614-619.

Nemoto, "Involvement of the system L amino acid transporter on uptake of S-nitroso-L-cysteine, an endogenous S-nitrosothiol, in PC12 cells", *Eur. J. Pharmacol.*, Jan. 1, 2003, vol. 458, Issues (1-2), pp. 17-24.

\* cited by examiner

Metformin

Cysteine

N-Acetyl-Cysteine
(NAC)

Hybrid I

Hybrid II

Hybrid II

METFORMIN-CYSTEINE PRODRUG

This patent application claims priority from U.S. Provisional Patent Application No. 61/325,204, entitled "Metformin-Cysteine Prodrug", filed Apr. 16, 2010, the specification of which is incorporated by reference herein.

BACKGROUND OF THE INVENTION

"A consensus statement from the American Diabetes Association and the European Association for the Study of Diabetes recommends metformin therapy as first-line therapy along with lifestyle modification to treat type 2 diabetes mellitus." Philbrick, Am. J. Health Syst. Pharm., 2009 Nov. 15; 66 (22):2017-23. According to Wikipedia, metformin was introduced to the United Kingdom in 1958, Canada in 1972, and the United States in 1995. Metformin is now believed to be the most widely prescribed anti-diabetic drug in the world. In the United States alone, more than 40 million prescriptions were filled in 2008 for its generic formulations. Because of metformin's status as a first line diabetic therapy, Bristol-Myers Squibb's diabetic drug Glucophage® brought in peak sales of $1.7 billion before its patent expired in 2000.

Metformin is a synthetic biguanadine having a molecular weight of about 165. Its molecular structure is shown in FIG. 1a.

It is believed that metformin improves glucose control in diabetics by increasing AMPK in hepatocytes, thereby providing control over glucose production.

Despite the effectiveness of metformin as a diabetes medication, it nonetheless suffers from some drawbacks. In particular, Marathe, Br. J. Clin., Pharmacol., 50, 325-332 (2000) has reported that, while metformin is effectively taken up in the small intestine, it is poorly absorbed in the colon. As a result, the time window for effective plasma concentrations of metformin is limited to about 6 hours. See, for example, FIG. 4 of US Patent Publication 2007-0154548 (Cheng Xiu), which reports that the window in which metformin is above ½ of its Cmax is only about 6 hours. Because of this narrow absorption window, metformin is typically presecribed to be taken about 2-3 times a day.

A number of attempts at improving the bioavailability of metformin involve providing metformin in an extended release dosage form that releases metformin in the colon. See, for example, US Patent Publication 2007275061; US Patent Publication 2007264331; and US Patent Publication 2009124702. However, these efforts to not improve the uptake efficiency of metformin in the colon.

Other attempts at improving the bioavailability of metformin involve providing metformin salts of lipophilic acids. See, for example, US Patent Publication 2003-0220301 (Lal).

US Patent Publication 2005-0158374 (Wong) discloses a complex comprised of metformin and a transport moiety, such as a fatty acid, is described. Wong reports that this complex has an enhanced absorption in the gastrointestinal tract, particularly the lower gastrointestinal tract. The complex, and compositions and dosage forms prepared using the complex, provide for absorption by the body of the drug through a period of ten to twenty-four hours, thus enabling a once-daily dosage form for metformin.

Other attempts have been made to improve the bioavailability of metformin by delivering it as a more lipophilic prodrug. In particular, the investigators in Huttunen, J. Med. Chem., 2009, 52, 14, 4142-4148 noted that N—S bonds may be cleaved by endogenous thiols and created sulfonamide prodrugs of metformin (FIG. 1c). The investigators report that the enhanced lipophilicity of these prodrugs appear to allow their passive diffusion into intestinal cells and that the metformin bioavailability increased from about 43% to about 60%.

SUMMARY OF THE INVENTION

It is noted that certain amino acids such as cysteine and NAC share a commonality with the Huttunen prodrugs in that each has a HS sulfur moeity. Accordingly, it is believed that a prodrug comprising metformin and cysteine may be made in a manner substantially similar to the Huttunen prodrugs, that is by achieving a N—S bond that includes the nitrogen of the $NH_2$ group in metformin and the sulfur of cysteine. This novel prodrug of the present invention is shown in FIG. 2.

In addition, while not wishing to be tied to a theory, it is believed that the resulting prodrug will have an improved intestinal uptake, superior even to the Huttunen prodrugs. In particular, it is noted that the prodrug of the present invention will possess an amino-cysteine moiety. It is further noted that s-nitroso-L-cysteine also possesses an amino-cysteine moiety, and that both Li, J. Biol. Chem., 280, 20, 20102-10 and Namoto, Eur. J. Pharmacol., 2003, Jan. 1, 458(1-2):17-24 report that s-nitroso-L-cysteine is efficiently transported by the LAT1 and LAT2 transporters. Therefore, it is reasonable to conclude that the amino-cysteine moiety of the prodrug of the present invention will allow for its transport in the LAT1 and LAT2 transporter system. Because the LAT1 and LAT2 transporters are important and effective transporters of amino acids in both the small intestine and colon, it is believed that the LAT-transportable prodrugs of the present invention will be effectively absorbed both in small intestine and in the colon. The increased absorption window provided by the present invention should result in highly sustained plasma concentrations of metformin, thereby increasing the effectiveness of the medication and allowing for a single daily dose.

Of note, Wang, J. Nutr., Biochem., 2002 October; 13(10): 625-633 reported that dietary supplementation of cysteine prodrugs to PM mice restored GSH levels in liver, lung, heart and spleen, but not in colon. Therefore, in that neither metformin nor cysteine appear to be taken up by the colon, it is indeed surprising that a prodrug comprising metformin and cysteine can be taken up by the colon.

Therefore, in accordance with the present invention, there is provided a metformin-cysteine prodrug.

In some embodiments, the metformin-cysteine prodrug comprises the structure of FIG. 2A (Hybrid I)

In some embodiments, the metformin-cysteine prodrug comprises the structure of FIG. 2B (Hybrid II)

DETAILED DESCRIPTION OF THE INVENTION

In addition to the increased bioavailability of the metformin-cysteine prodrug of the present invention, it is further noted that the cysteinic portion of the prodrug may also provide benefit to the diabetic patient.

First, it is believed that the cysteine portion of the prodrug forms a disulfide with GSH to produce Cy-LLGSH. This molecule has been characterized as a prodrug that is cleaved back into cysteine and GSH moieties. See Cacciatoreo, *Molecules,* 2010, pp 1242-1264.

Second, it has been widely reported in the literature that cysteine is regarded as the rate-limiting building block for the tripeptide glutathione (GSH). Dilger, *J. Anim. Sci.* 2007, 85:1712-18. Since GSH is well known as one of the most potent endogenous antioxidants, it is believed that the cysteine portion of the prodrug will help ameliorate reactive oxygen species in type II diabetes.

Third, there have been several clinical trials assessing the efficacy of NAC for type II diabetic patients. See, for example, NCT00556465; Masha, *J. Endocrinol. Invest.,* 2009 April:32(4) 352-6; and Saklayan, *J Investig Med.,* 2010 January; 58(1):28-31.

Fourth, the Cy-LLGSH prodrug produced by metabolism of the novel prodrug has been shown to be "highly effective" in protecting mice against acetaminophen-induced hepatotoxicity. The authors credit the success of the treatment to an enzymatic process that provides glutathione directly to the cells. Berkeley, *J. Biochem. Molec. Toxicology,* 17, 2, 2003, 95-97

Finally, de Oliveira, *Hepatology Research,* 2008, 38, 159-165 reports that the combination of metformin and NAC provided the significant amelioration of the complications of non-alcoholic fatty liver disease in human patients. de Oliveira further reports that neither metformin nor NAC alone provided any significant benefits to NASH patients.

Figure 1A:
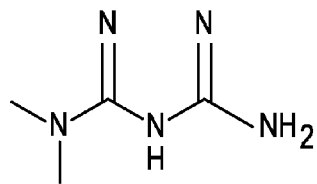
FIG. 1a provides the molecular structure of metformin.
Figure 1B:
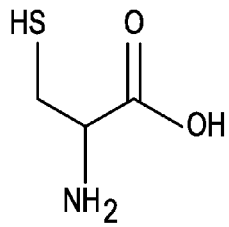
FIG. 1b provides the molecular structure of cysteine.
Figure 1C:
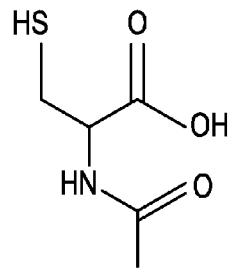
FIG. 1c provides the molecular structure of n-acetylcysteine (NAC).
Figure 2A:
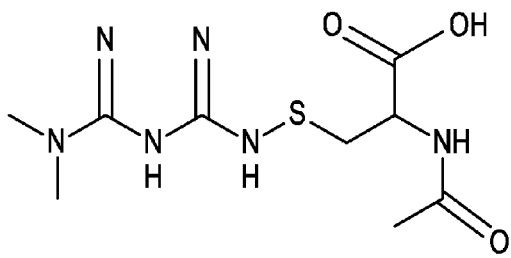
FIGS. 2a and 2b provide the molecular structures of two molecules of the present invention, Hybrids I and II, respectively.
Figure 2B:
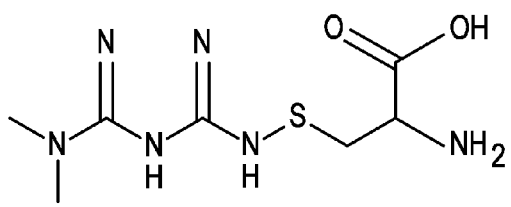
Figure 3:
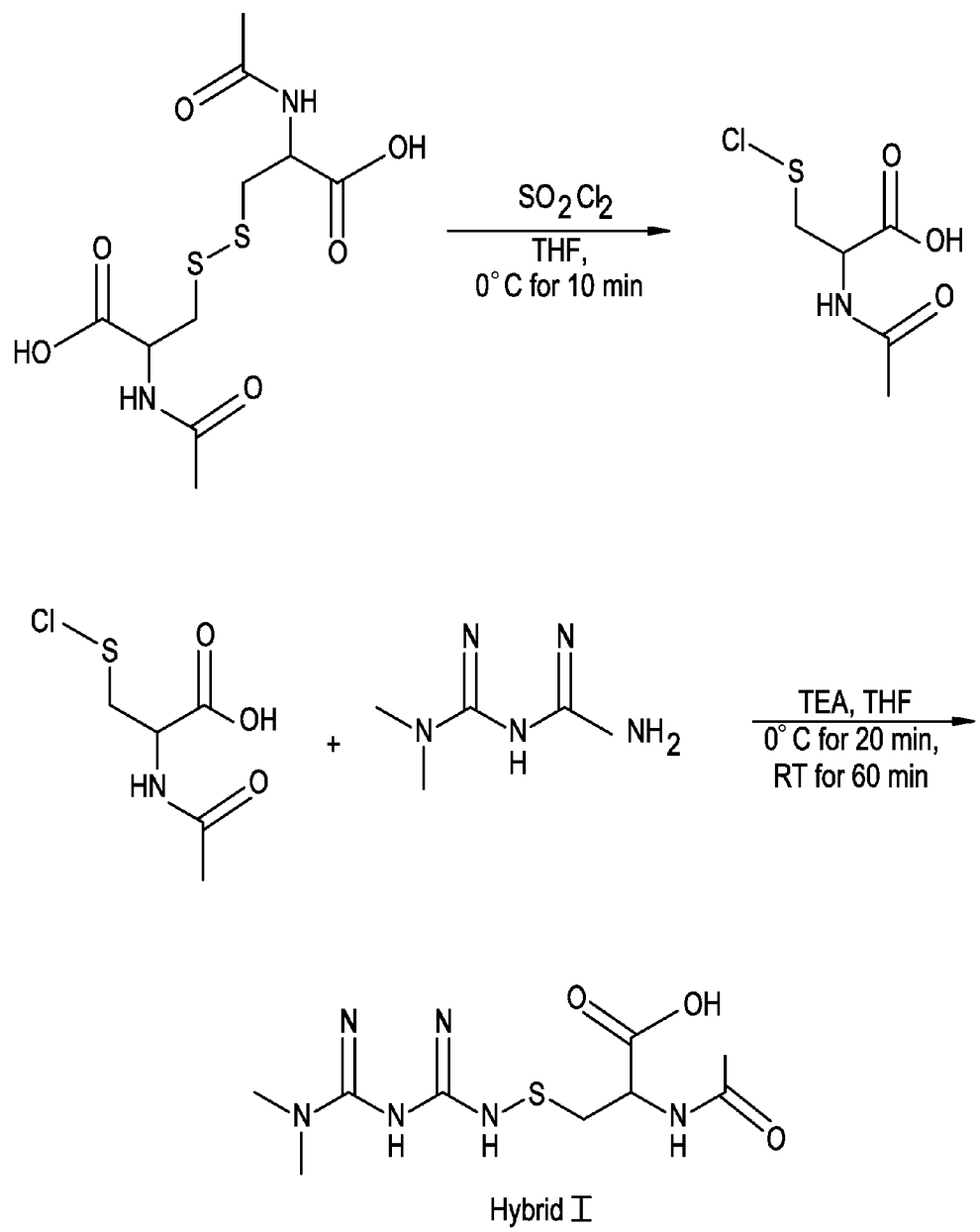
FIGS. 3 and 4 disclose methods of making the present invention in accordance with the Guarino approach.
Figure 4:
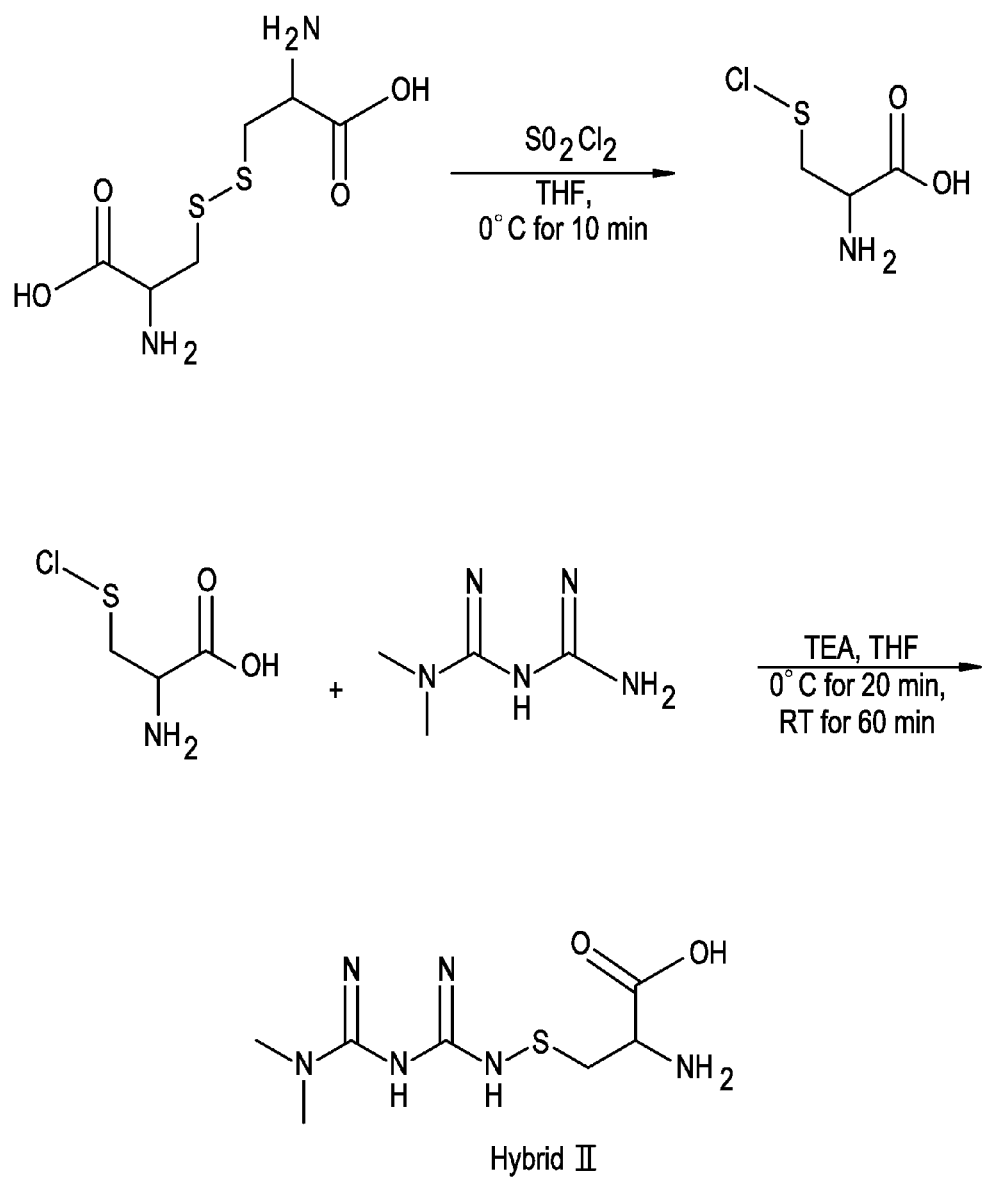

In order to make the novel molecules of the present invention, standard organic chemistry techniques for sulfenamide synthesis may be used. In one approach, the techniques of sulfenamide synthesis disclosed in Scheme 2 of Guarino, *Bioorg. & Medicinal Chemistry Letters* 17, (2007) 4910-13 are used. Prophetic examples of the Guarino approach are provided in FIGS. 3a and 3b. Barton, *J. Org. Chem.,* 56, 23, 1991 6702-4 teaches that methods of sulfonamide synthesis such as Guarino's that react chlorothiols with amides can reliably form sulfenamides provided that the reaction is carried out under high pH and with the use of a nonpolar aprotic solvent (such as THF).

Exemplary Dosage Forms and Methods of Use

It is believed that the novel molecules described above provide an enhanced absorption rate in the G.I. tract, and in particular in the lower G.I. tract. Dosage forms and methods of treatment using these molecules and their increased colonic absorption will now be described. It will be appreciated that the dosage forms described below are merely exemplary.

A variety of dosage forms are suitable for use with the metformin-cysteine hybrid. As discussed above, a dosage form that provides once daily dosing to achieve a therapeutic efficacy for at least about 15 hours, more preferably for at least 18 hours, and still more preferably for at least about 20 hours, is desired. The dosage form may be configured and formulated according to any design that delivers a desired dose of metformin. Typically, the dosage form is orally administrable and is sized and shaped as a conventional tablet or capsule. Orally administrable dosage forms may be manufactured according to one of various different approaches. For example, the dosage form may be manufactured as a diffusion system, such as a reservoir device or matrix device, a dissolution system, such as encapsulated dissolution systems (including, for example, "tiny time pills", and beads) and matrix dissolution systems, and combination diffusion/dissolution systems and ion-exchange resin systems.

The dose administered is generally adjusted in accord with the age, weight, and condition of the patient, taking into consideration the dosage form and the desired result. In general, the dosage forms and compositions of the metformin-cysteine hybrid are administered in amounts recommended for metformin HCl (Glucophage®, Bristol-Myers Squibb Co.) as set forth in the Physician's Desk Reference. For example, oral dosage of metformin HCl is individualized on the basis of effectiveness and tolerance, while not exceeding the maximum daily recommended dose of 2550 mg in adults and 2000 mg in pediatric patients. Metformin HCl is typically administered in divided doses with meals and is often initiated at a low dose, typically of about 850 mg/day, with gradual escalation to permit identification of a minimum therapeutically effective amount required for an individual's anti-hyperglycemic activity. Thus, in one embodiment, a dosage form that provides a daily metformin dose of between 500-2550 mg is provided, where the metformin is provided in the form of a metformin-cysteine hybrid.

In another aspect, the invention contemplates administering a metformin-cysteine hybrid in combination with a second therapeutic agent, for treatment of hyperglycemia and for management of weight, particularly in Type II diabetic subjects. Preferred second therapeutic agents are those useful in the treatment of obesity, diabetes mellitus, especially Type II diabetes, and conditions associated with diabetes mellitus.

Exemplary second therapeutic agents include, but are not limited to, compounds classified as an alpha glucosidase inhibitor, a biguanide (other than metformin), an insulin secretagogue, an antidiabetic agent, or an insulin sensitizer. Exemplary alpha glucosidase inhibitors include acarbose, emiglitate, miglitol, voglibose. A suitable antidiabetic agent is insulin. Biguanides include buformin and phenformin. Suitable insulin secretagogues include sulphonylureas, such as glibenclamie, glipizide, gliclazide, glimepiride, tolazamide, tolbutamine, acetohexamide, carbutamide, chlorpropamide, glibornuride, gliquidone, glisentide, glisolamide, glisoxepide, glyclopyamide, repaglinide, nateglinide, and glycyclamide. Insulin sensitizers include PPAR-gamma agonist insulin sensitizers (see WO97/31907), such as 2-(1-carboxy-2-{4-2-(5-methyl-2-phenyl-oxazol-4-yl)-ethoxy]-phenyl-ethyla-mino)-benzoic acid methyl ester and 2(S)-(2-benzoyl-phenylamino)-3-4-[2-(5-methyl-2-phenyl-oxazol-4-yl)-ethoxy]-phenyl}-propionic acid.

The second therapeutic agent is preferably an anti-diabetic compound, such as insulin signaling pathway modulators, like inhibitors of protein tyrosine phosphatases (PTPases), non-small molecule mimetic compounds and inhibitors of glutamine-fructose-6-phosphate amidotransferase (G FAT), compounds influencing a dysregulated hepatic glucose production, like inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK), pyruvate dehydrogenase kinase (PDHK) inhibitors, insulin sensitivity enhancers, insulin secretion enhancers, .alpha.-glucosidase inhibitors, inhibitors of gastric emptying, insulin, and .alpha.sub.2-adrenergic antagonists, or the pharmaceutically acceptable salts of such a compound and optionally at least one pharmaceutically acceptable carrier; for simultaneous, separate or sequential use, particularly in the prevention, delay of progression or treatment of conditions mediated by DPP-IV, in particular conditions of impaired glucose tolerance (IGT), conditions of impaired fasting plasma glucose, metabolic acidosis, ketosis, arthritis, obesity and osteoporosis, and preferably diabetes, especially type 2 diabetes mellitus. Such a combination is preferably a combined preparation or a pharmaceutical composition.

In a combined treatment method, the metformin-cysteine hybrid and the second therapeutic agent are administered simultaneously or sequentially, by the same or different routes of administration.

In a preferred embodiment, the second therapeutic agent is a dipeptidyl peptidase IV (DPP-IV) inhibitor. Dipeptidyl peptidase IV is a post-proline/alanine cleaving serine protease found in various tissues in the body, including kidney, liver, and intestine. The protease removes the two N-terminal amino acids from proteins having proline or alanine in the position 2. DPP-IV can be used in the control of glucose metabolism because its substrates include the insulinotropic hormones glucagons like peptide-1 (GLP-1) and gastric inhibitory peptide (GIP). GLP-1 and GIP are active only in their intact forms; removal of their two N-terminal amino acids inactivates them (Holst, J. et al., Diabetes, 47:1663 (1998)).

Thus, inhibitors of DPP-IV have been described, for example, in U.S. Pat. Nos. 6,124,305; 6,107,317; and in PCT Publication Nos. WO99/61431; WO98/19998; WO95/15309; WO98/18736. The inhibitors can be peptidic or non-peptidic, such as 1 [2-(5-cyanopyridin-2yl)aminoethylamino-]acetyl-2-cyano-(S)-pyrrolidine and (2S)-1-[(2S)-2-amino-3,3-dimethylbutan-oyl]-2-pyrrolidinecarbonitrile.

A method for treating a subject having Type II diabetes is contemplated, where the subject is treated with a DPP-IV inhibitor in combination with a metformin-cysteine hybrid. The combined agents produces a greater beneficial effect than achieved for either agent alone or for a combination of a DPP-IV inhibitor and metformin. The metformin-cysteine hybrid is preferably administered orally in a once-daily dosage form, to take full advantage of the enhanced colonic absorption provided by the hybrid. The DPP-IV inhibitor can be administered by any route suitable for the compound and the patient.

In one embodiment, the combined treatment regimen is for use in reducing or preventing body weight gain in overweight or obese patients with Type II diabetes. It has been recently shown that a combination therapy of metformin with DPP-IV inhibitor leads to reduced food intake and body weight gain in Zucker fa/fa rats (Yasuda, N. et al., J. Pharmacol. Experimental Therap., 310(2):614 (2004)). The invention provides an improved combination regimen by administering metformin as a metformin-cysteine hybrid to achieve an enhanced colonic absorption.

An effective dosage is defined in the present invention as the amount of a compound that prevents or ameliorates adverse conditions or symptoms of disease(s) or disorder(s) being treated. The amount to be administered to a patient and the frequency of administration to the subject can be readily determined by one of ordinary skill in the art by the use of known techniques and by observing results obtained under analogous circumstances. In determining the effective dosage, a number of factors are considered by the attending diagnostician, including but not limited to, the potency and duration of action of the compounds used; the nature and severity of the illness to be treated as well as the sex, age weight, general health and individual responsiveness of the patient to be treated, and other relevant circumstances.

The compositions of the invention are preferably administered enterally or parenterally (parenteral administration includes subcutaneous, intramuscular, intradermal, intramammary, intravenous, and other administrative methods known in the art), or better still orally, although other routes of administration, for instance such as rectal administration, are not excluded.

For preparing oral pharmaceutical compositions from the compounds of this invention, inert, pharmaceutically acceptable carriers can be either solid or liquid. Solid form preparations include powders, tablets, coated tablets, dragees, troches, lozenges, dispersible granules, capsules, and sachets. Compositions for oral use may be prepared according to any method known in the art of manufacture of pharmaceutical compositions.

A solid carrier can be one or more substances which may also act as diluents, flavoring agents, solubilizers, lubricants, suspending agents, binders, or tablet disintegrating agents. It can also be an encapsulating material. In powders, the carrier is a finely divided solid, which is in admixture with the finely divided active component. In tablets, the active compound is mixed with the carrier having the necessary binding properties in suitable proportions and compacted in the shape and size desired. Suitable carriers include, for example, inert diluents, such as magnesium carbonate, calcium stearate, magnesium stearate, talc, lactose, sugar, pectin, dextrin, starch, tragacanth, methyl cellulose, sodium carboxymethyl cellulose, and the like.

The present invention also includes the formulation of metformin-cysteine hybrid and orlistat with encapsulating material as a carrier providing a capsule in which the hybrid and orlistat (with or without other carriers) are surrounded by a carrier, which is thus in association with the hybrid and orlistat. In a similar manner, sachets are also included. Tablets, powders, sachets, and capsules can be used as solid dosage forms suitable for oral administration.

The tablets may be uncoated or coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules in which the active compounds are mixed with inert solid diluent, for example, calcium carbonate, calcium phosphate or kaolin, or as soft gelatin capsules in which the active compounds are present as such, or mixed with water or an oil medium, for example, arachid oil, liquid paraffin, or olive oil.

Aqueous suspensions can be produced that contain the active compounds in admixture with excipients suitable for the manufacture of aqueous suspensions. Such excipients include suspending agents, such as sodium carboxymethylcellulose, methylcellulose, hydroxypropylmethylcellulose, sodium alginate, polyvinylpyrrolidone gum tragacanth and gum acacia; dispersing or wetting agents e.g. naturally-occurring phosphatides, such as lecithin, condensation products of an alkylene oxide with fatty acids, such as polyoxyethylene stearate, condensation products of an alkylene oxide with fatty acids, such as polyoxyethylene stearate, condensation products of ethylene oxide with long chain aliphatic alcohols, such as heptadecaethyleneoxycetanol, condensation products of ethylene oxide with partial esters derived from fatty acids and a hexitol, such as polyoxyethylene sorbitol monooleate, or condensation products of ethylene oxide with partial esters derived from fatty acids and hexitol anhydrides, such as polyoxyethylene sorbitan monooleate.

The aqueous suspensions may also contain one or more preservatives, for example, ethyl or n-propyl p-hydroxybenzoate, one or more coloring agents, one or more flavoring agents, one or more sweetening agents.

Oily suspensions may be formulated by suspending the active compounds in an omega-3 fatty acid, a vegetable oil, for example arachid oil, olive oil, sesame oil or coconut oil, or in a mineral oil such as liquid paraffin. The oily suspensions may contain a thickening agent, for example, beeswax, hard paraffin or cetyl alcohol.

Sweetening agents and flavoring agents may be added to provide a palatable oral preparation, which may be preserved by the addition of an antioxidant such as ascorbic acid.

Dispersible powders and granules suitable for the preparation of an aqueous suspension by the addition of water provide the active compounds in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs containing the novel combination may be formulated with sweetening agents. Such formulations may also contain a demulcent, a preservative and flavoring and coloring agents.

Liquid form preparations include solutions, suspensions and emulsions suitable for oral administration. Aqueous solutions for oral administration can be prepared by dissolving the active compounds in water and adding suitable flavoring agents, coloring agents, stabilizers, and thickening agents as desired. Ethanol, propylene glycol and other pharmaceutically acceptable non-aqueous solvents may be added to improve the solubility of the active compounds. Aqueous suspensions for oral use can be made by dispersing the finely divided active compounds in water together with a viscous material such as natural or synthetic gums, resins, methyl cellulose, sodium carboxymethyl cellulose, and other suspending agents known in the pharmaceutical formulation art.

Preferably, the pharmaceutical composition is in unit dosage form. In such form, the preparation is divided into unit doses containing appropriate amounts of the active compounds. The unit dosage form can be a packaged preparation, the package containing discrete amounts of the preparation, for example, packeted tablets, capsules, and powders in vials or ampoules. The unit dosage form can also be a capsule, cachet, or tablet itself, or it can be the appropriate number of any of these packaged forms.

Formulations developed for the metformin-cysteine hybrid can be used for the pharmaceutical composition of the invention containing the hybrid and orlistat. Such formulations are described in the following patents: gastric retentive (U.S. Pat. No. 6,340,475=WO 9855107 and U.S. Pat. No. 6,120,803=WO 9907342), controlled-release metformin composition (U.S. Pat. No. 6,790,459=WO 0236100), controlled-release with unitary core (U.S. Pat. No. 6,099,859=WO 9947125), treatment with 400 mg or below of metformin (U.S. Pat. No. 6,100,300), novel salts of metformin (U.S. Pat. No. 6,031,004=WO 9929314), biphasic controlled-release delivery system (U.S. Pat. No. 6,475,521=WO 9947128), metformin preparation (U.S. Pat. No. 5,955,106=WO 9608243), controlled-release (WO 0103964 and US 2004/175424=WO 0239984), metformin tablet (US 2003/021841=WO 03004009), sustained-release composition (US 2002/132002=WO 02067905), controlled-release composition (U.S. Pat. No. 6,491,950=WO 0211701), gastroretentive (WO 0006129), solid carriers for improved delivery (U.S. Pat. No. 6,923,988=WO 0137808), coating for sustained-release composition (U.S. Pat. No. 6,946,146=WO 02085335), modified-release composition (US 2004/213844=WO 03002151), liquid formulation of metformin (WO 0247607), controlled-release device (U.S. Pat. No. 6,960,357=WO 02094227), metformin quick release tablet (JP 2002326927). Among these formulations, the metformin once a day formulation is preferred.

The compositions of the invention can also be administered parenterally either subcutaneously, or intravenously, or intramuscularly, or intrasternally, or by infusion techniques, in the form of sterile injectable aqueous or olagenous suspensions. Such suspensions may be formulated according to the known art using those suitable dispersing or wetting agents and suspending agents which have been mentioned above, or other acceptable agents. The sterile injectable preparation may also be a sterile injectable solution or suspension in a non-toxic parenterally acceptable diluent or solvent, for example as a solution in 1,3-butanediol. Among the acceptable vehicles and solvent that may be employed, water, Ringer's solution and isotonic sodium chloride solution may be mentioned. In addition, sterile, fixed oils are conventionally employed as a solvent or suspending medium. For this purpose, any bland fixed oil may be employed including synthetic mono- or diglycerides. In addition, n-3 polyunsaturated fatty acids may find use in the preparation of injectables.

The compositions of the invention can also be administered by inhalation, in the form of aerosols or solutions for nebulizers, or rectally in the form of suppositories prepared by mixing the drug with a suitable non irritating excipient, which is solid at ordinary ambient temperature but liquid at the rectal temperature and will therefore melt in the rectum to release the drug. Such materials include cocoa butter and polyethylene glycols.

Preferably, the composition is a controlled-release composition.

Daily dosages can vary within wide limits and will be adjusted to the individual requirements in each particular case. In general, for administration to adults, an appropriate daily dosage has been described above, although the limits that were identified as being preferred may be exceeded if expedient. The daily dosage can be administered as a single or divided dose.

The amount of each compound to be administered will depend on a number of factors including the age of the patient, the severity of the condition and the past medical history of the patient. Each unit dose generally contains (1) from about 100 to 1000 mg of metformin and/or (2) from about 50 to about 720 mg, preferably about 120 to about 360 mg, of orlistat. Typical unit doses preferably contain 500 mg, 850 mg or 1000 mg of metformin (850 mg being especially preferred) and/or 120 mg of orlistat. It will however be appreciated that formulations containing doses of metformin and/or orlistat which are bioequivalent to the preferred doses mentioned above, are within the scope of the invention. For example, a formulation containing a dose of metformin which is bioequivalent to the dose of the Glucophage® 850 formulation, is contemplated.

When the pharmaceutical composition comprises a fibrate, each unit dose generally contains from about 10 to about 1000 mg, preferably about 50 to 600 mg, more preferably about 50 to about 200 mg, of fibrate. When the pharmaceutical composition comprises a statin, each unit dose generally contains from about 0.1 to 100 mg of statin, e.g. 0.1, 0.3, 0.8, 1, 2, 5, 10, 20, 40 or 80 mg of statin.

The present invention further relates to kits that are suitable for use in performing the methods of treatment described above. In one embodiment, the kit contains (i) one or more unit doses of the hybrid, (ii) one or more unit doses of orlistat, (iii) optionally one or more unit doses of a fibrate, and (iv) optionally one or more unit doses of a statin, for a simultaneous or sequential administration, in amounts sufficient to carry out the methods of the present invention.

In some embodiments, the molecule of the present invention can be used for treating a patient having Alzheimer's Disease or mild cognitive impairment (MCI). Both metformin (Kickstein, *Proc Natl Acad Sci USA*, 2010 Dec. 14; 107(50):21830-5) and NAC (McCaddon, CNS Spectr. 2010 January; 15(1 Suppl 1):2-5;) have been discussed as potential treatment for Alzheimer's Disease.

I claim:

1. A metformin-cysteine conjugate having the following structure:

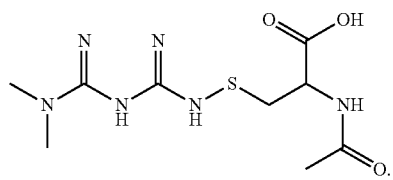 [SMILES: CC(=O)NC(CSNC(=N)NC(=N)N(C)C)C(=O)O]

2. A metformin-cysteine conjugate having the following structure:

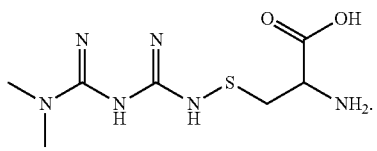 [SMILES: CN(C)C(=N)NC(=N)NSCC(N)C(=O)O]

* * * * *